United States Patent [19]

Lerman

[11] Patent Number: 4,832,010
[45] Date of Patent: May 23, 1989

[54] ORTHOPEDIC SUPPORTS AND MATERIAL FOR MAKING SAME

[76] Inventor: Max Lerman, 1950 Carla Ridge, Beverly Hills, Calif. 90210

[21] Appl. No.: 122,553

[22] Filed: Nov. 12, 1987

Related U.S. Application Data

[63] Continuation of Ser. No. 743,687, Jun. 11, 1985, abandoned.

[51] Int. Cl.⁴ .............................................. A61F 13/00
[52] U.S. Cl. ..................................... 128/165; 128/77; 128/80 C; 128/80 H; 2/2; 2/24
[58] Field of Search ................. 128/80 C, 80 B, 80 H, 128/155, 157, 165, 166, 80; 2/2, DIG. 1, DIG. 7, 24

[56] References Cited

U.S. PATENT DOCUMENTS

| | | | |
|---|---|---|---|
| 2,570,182 | 10/1951 | Daly et al. ............................ 264/55 |
| 2,653,601 | 9/1953 | Morrison .............................. 128/165 |
| 2,976,539 | 3/1961 | Brown, Jr. .................................... 2/2 |
| 3,092,110 | 6/1963 | Duensing ........................ 128/165 X |
| 3,451,232 | 6/1969 | Belzidsky . |
| 3,600,717 | 8/1971 | McKeehan . |
| 3,990,440 | 11/1976 | Gaylord ............................. 128/165 |
| 3,991,424 | 11/1976 | Prahl . |
| 4,043,058 | 8/1977 | Hollister et al. ...................... 36/102 |
| 4,084,586 | 4/1978 | Hettick ............................... 128/165 |
| 4,153,054 | 5/1979 | Boone ................................. 128/157 |
| 4,294,240 | 10/1981 | Thill . |
| 4,470,411 | 9/1984 | Hoyt, Jr. ............................. 128/165 |
| 4,516,572 | 5/1985 | Schlein . |

Primary Examiner—Richard J. Apley
Assistant Examiner—Paul Prebilic
Attorney, Agent, or Firm—Christie, Parker & Hale

[57] ABSTRACT

Orthopedic supports are made from a flexible, resilient composite material which includes a base layer of a flexible, closed cell elastomeric material such as neoprene rubber in thin sheet form, with a multiplicity of relatively large air holes extending through the depth of the sheet and dispersed across the surface of the sheet. A skin-protecting first layer of a soft, flexible stretchable porous knitted fabric is adhered to a first face of the base layer. A protective second layer of a flexible, stretchable porous knitted fabric is adhered to the second face of the base layer. The composite material is porous to air and water passing through the depth of the composite layer. Orthopedic supports made from the material are sufficiently elastic to provide compression around a body part supported by the composite material in its stretched condition. The composite material is sufficiently porous to ventilate the supported body part during use such that elasticity and support is provided while heat discomfort and perspiration are prevented.

29 Claims, 2 Drawing Sheets

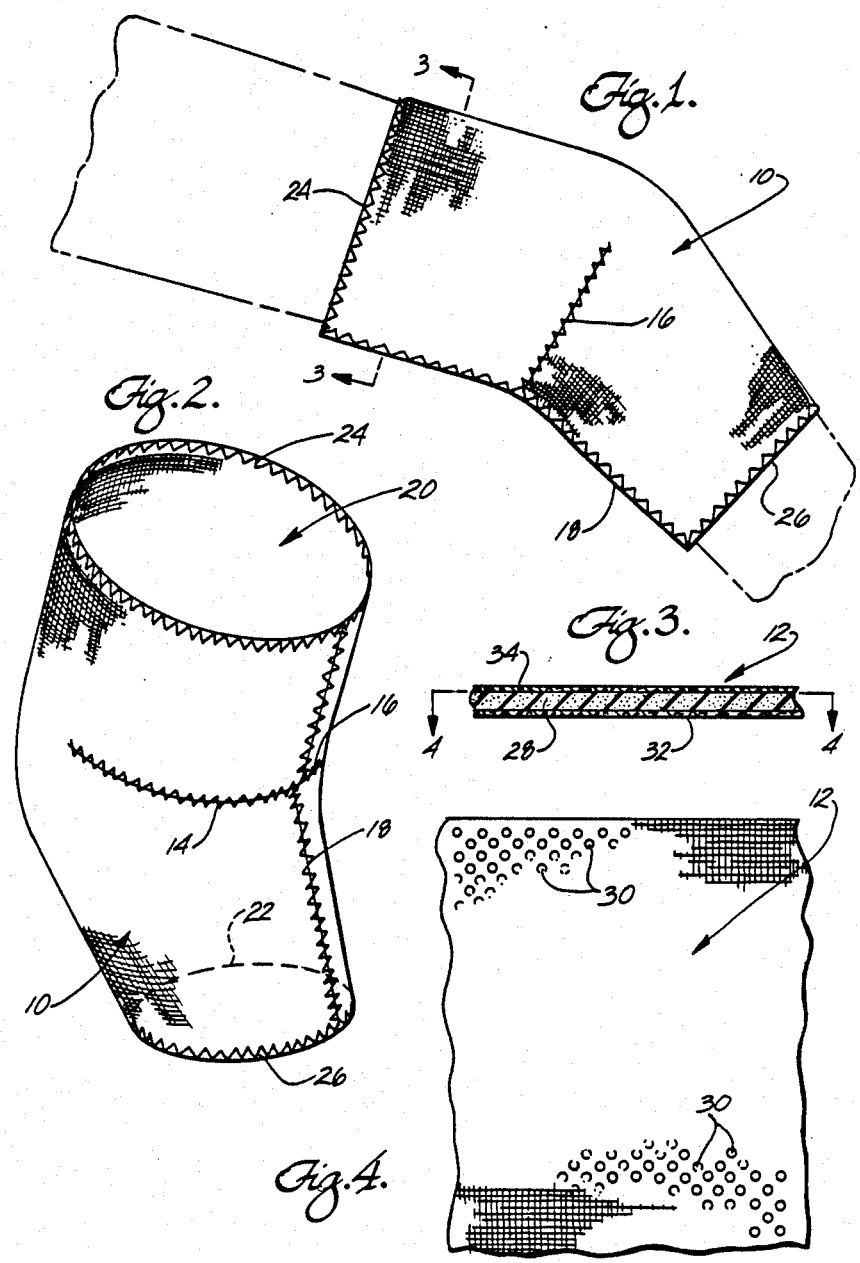

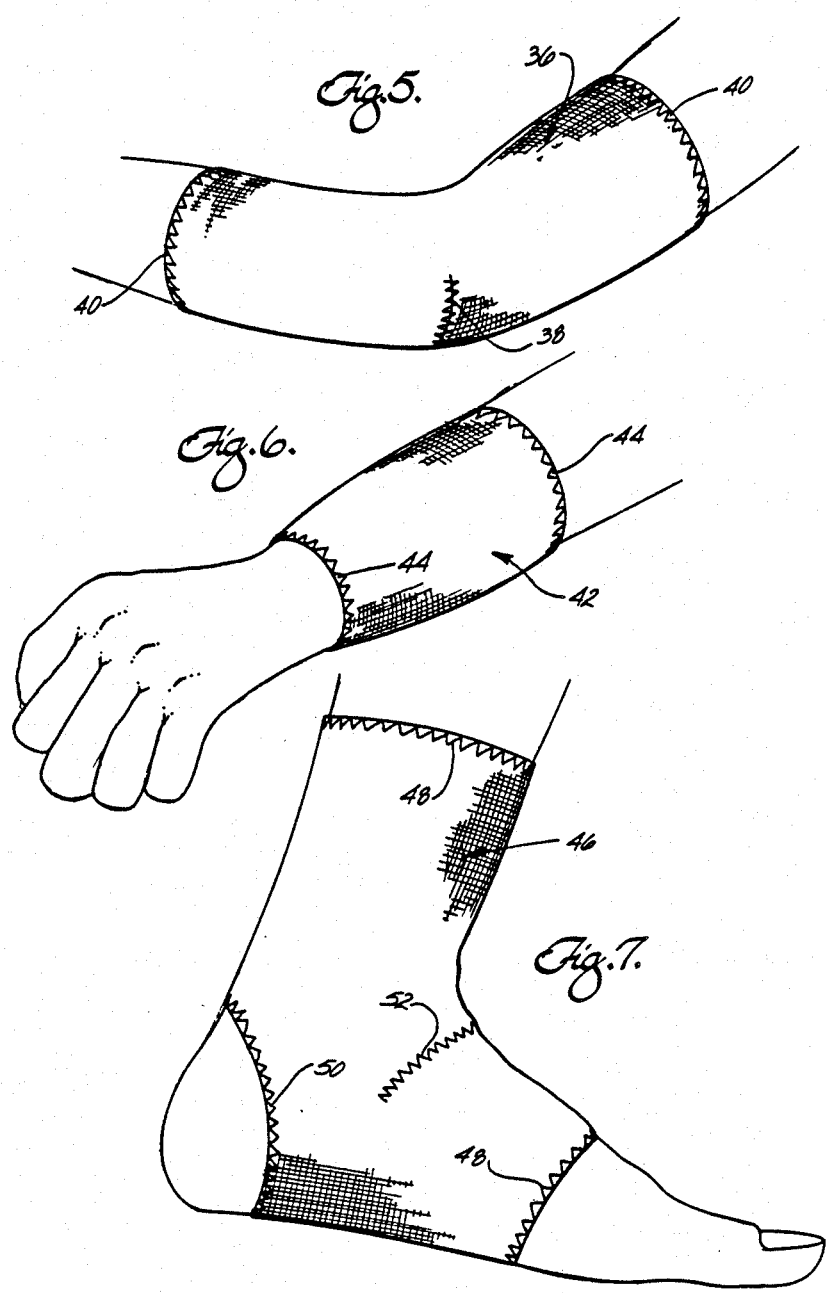

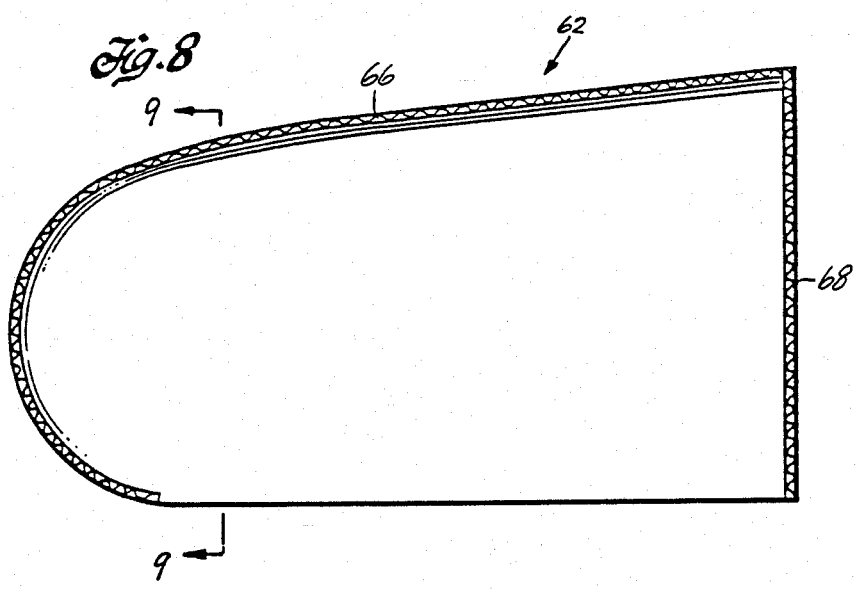
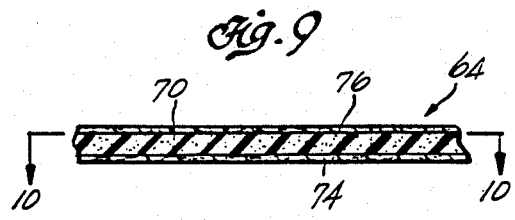
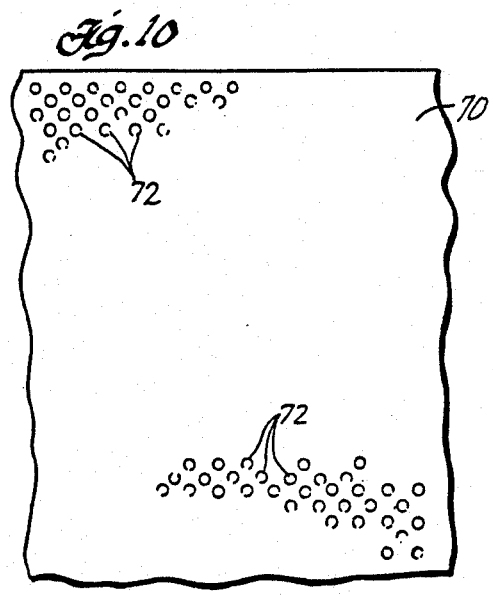

ORTHOPEDIC SUPPORTS AND MATERIAL FOR MAKING SAME

CROSS-REFERENCE TO RELATED APPLICATIONS

This ia continuation of application Ser. No. 743,687 filed June 11, 1985, now abandoned.

FIELD OF THE INVENTION

This invention relates to a composite material for use in making orthopedic supports having improved properties during use. More particularly, the composite material provides a novel combination of elasticity and good compression support, shear resistance, and porosity to air and water sufficient to avoid heat discomfort and perspiration of the user during prolonged periods of use.

BACKGROUND OF THE INVENTION

Orthopedic supports are available in many forms. A common orthopedic support is a rigid knee brace worn by persons who suffer knee instabilities and by those engaged in sporting activities to prevent injuries to the knee. A common purpose of the knee brace is to provide exterior support for the knee to prevent any unnatural movements of the knee joints which could injure or reinjure the knee ligaments, while allowing the normal swinging movement of the knee joint. Such knee braces are commonly used for post-operative patients who have had knee surgery. These knee braces commonly include metal bars and pivot joints to provide a rigid means of support. Such knee braces are sold by a physician's prescription only and require a skilled orthotist to fit them properly to the patient.

Other orthopedic supports are the so-called "soft supports" which are sold in drug stores, hospitals and doctors' offices. The soft supports provide a modest amount of support for an injured joint. These types of supports do not include rigid metal bars or stays, but are simply made from a soft, stretchable material. They are often purchased without a prescription or the need for skilled professional fitting. The soft orthopedic supports have been used for a number of years and have been commonly available as supports for the knee, ankle, thigh, wrist, elbow, chest or lower back. These soft orthopedic supports are normally worn for sprains and strains, arthritis, tendonitis, bursitis, inflammation, or to reduce discomfort during post-operative use or to treat post-trauma discomfort.

The soft-orthopedic supports are often made from neoprene rubber (i.e. polychloroprene). This material is desirable because of its combination of favorable properties useful in orthopedic supports. Neoprene rubber has good elasticity and a relatively high density, properties which combine to provide good compression support and resistance to shear forces.

Neoprene rubber is a closed cell material and therefore does not dissipate heat very well during use. Its closed cell characteristics can be useful in retaining heat during use by reflecting emitted heat back into the bones and joints of the affected area. This localized concentration of heat can aid venous flow, help reduce edema, and make the soft tissues less susceptible to injury.

Although use of neoprene rubber in orthopedic supports can be useful because of its ability to concentrate heat, the natural tendency of the closed cell material to prevent heat dissipation creates problems for the user. The neoprene rubber supports are stretched when applied so that the material can compress around the affected area. This tight compression fit, combined with the high density of the material and the lack of air circulation and dissipation through the material, causes heat discomfort and perspiration and often leads to heat rashes. Prolonged use of such neoprene rubber supports can cause the user to perspirate constantly, causing discomfort to such a degree that the user often stops wearing the support prematurely. In effect, the material itself dictates the length of time that the orthopedic supports can be worn. It is not uncommon for users to stop wearing such supports after about one to two hours.

Replacing the closed cell neoprene rubber with an open cell material does not provide an acceptable solution to the heat discomfort problem. Open cell materials, such as sponge rubber or plastic foam materials such as high density polyester or polyurethane foams, are materials characterized by their ability to "breathe". That is, they are porous to air and water. Such materials can ensure good air circulation and good heat dissipation and absorption of body fluids during use. However, such open cell materials do not inherently possess the high density necessary for the materials to provide sufficient compressive strength to serve as an orthopedic support.

Thus, there is a need for an orthopedic support having sufficient elasticity and density to offer a necessary level of compression support, while also dissipating heat during use sufficient to avoid undue perspiration and heat discomfort during prolonged use of the support.

SUMMARY OF THE INVENTION

Briefly, this invention provides a flexible, resilient composite material for use in making elastic orthopedic supports for supporting a body part by compression. The composite material includes a base layer of a flexible, elastomeric closed cell material in thin sheet form having a multiplicity of air holes extending through the depth of the sheet and dispersed across the surface of the sheet. A skin-protecting first layer of a soft, flexible, resilient porous fabric is adhered to a first face of the base layer. A protective second layer of a flexible, resilient porous fabric is adhered to an opposite second face of the base layer. The composite material is porous to air and water passing through the depth of the composite material. When used as an orthopedic support, it allows sufficient air circulation to avoid perspiration and heat discomfort during prolonged used. The air holes in the elastomeric base layer of closed cell material combine with the porous first and second layers of knitted fabric to enhance air circulation and reduce heat build-up during use. The high density of the closed cell material provides sufficient compression support for the affected area during use. The first and second knitted fabric layers provide elasticity on opposite sides of the elastomeric base layer. They reinforce the strength of the composite material to overcome any level of elasticity or strength lost because of the added hole pattern in the elastomeric base layer. Experimental use of orthopedic supports made from this composite material has demonstrated substantial improvements in absence of perspiration and attendant heat discomfort from long periods of use.

These and other aspects of the invention will be more fully understood by referring to the following detailed description and the accompanying drawings.

DRAWINGS

FIG. 1 is a side elevation view semi-schematically illustrating a knee support made from an orthopedic material according to principles of this invention.

FIG. 2 is a semi-schematic perspective view of the knee support shown in FIG. 1.

FIG. 3 is a cross-sectional view schematically illustrating components of a composite orthopedic material of this invention.

FIG. 4 is a fragmentary plan view illustrating a perforated closed cell elastomeric layer of the composite material.

FIG. 5 is a perspective view illustrating an elbow support made from the composite material.

FIG. 6 is a perspective view illustrating a wrist support made from the composite material.

FIG. 7 is a side view illustrating an ankle support made from the composite material.

DETAILED DESCRIPTION

FIGS. 1 and 2 illustrate a knee support 10 made from an orthopedic material according to principles of this invention. The orthopedic material is illustrated in FIGS. 3 and 4. The knee support is a soft orthopedic support made entirely from a flexible, resilient composite material 12 shown in flat form in FIGS. 3 and 4. The flat form composite material is folded over and seamed to form the finished tubular knee support 10 illustrated in FIGS. 1 and 2.

Referring to FIGS. 1 and 2, a piece of the composite material 12 in flat sheet form is folded over on itself and cut inwardly from the middle of the overlapping long edges on the side opposite the fold. The cut-out portion is a V-shaped region extending from the overlapping long edges toward the fold at the opposite side. The overlapping edges along the central region of the folded material are fastened by left and right stitched seams 14 and 16, respectively. The overlapping long edges on the opposite side of the fold are fastened by a long upright seam 18. This produces an angular knee support of generally tubular form having an open top 20 and an open bottom 22. Peripheral stitching 24 at the upper edge and similar peripheral stitching 26 at the bottom edge provide finished edges for the completed knee support.

The materials which comprise the composite material 12 are understood best by referring to FIGS. 3 and 4. The composite material includes a flexible and foldable elastomeric base layer 28 in thin sheet form made from a closed cell material. The preferred elastomeric closed cell material is neoprene rubber. The neoprene rubber layer 28 is perforated by a multiplicity of holes 30 dispersed across the surface of the neoprene rubber layer and extending through the entire depth of the neoprene rubber layer so that fluids can pass through the holes from one side of the layer to the other. The perforations 30 are not shown in FIG. 3 for simplicity. The hole pattern shown in FIG. 4 is somewhat exaggerated in relative size, but illustrates the preferred technique of forming the holes in a uniform pattern in which all holes are of uniform diameter and spaced apart uniformly across the face of the neoprene rubber layer. In one embodiment, the neoprene rubber layer has a 0.090 inch hole diameter with ¼ inch on-center diagonal spacing between adjacent holes in the uniform pattern. Preferred neoprene materials are sold by Rubatex Corporation, Bedford, Va., and sold under stock numbers G-231-N, G-207-N, or R-411-N. These materials have a density in the range of about 10 to about 30 pounds per cubic foot. In experimental tests, these materials have provided good results when used in orthopedic supports. The size of the holes and their distribution across the face of the neoprene rubber layer are such that the holes can provide immediate heat dissipation during use of the material in a composite orthopedic support. The holes must not be so large or spaced so close together that the overall elasticity or density of the neoprene rubber layer is reduced beyond the ability of the material to provide sufficient orthopedic compression support during use. A useful hole pattern is one in which the total area of the holes in a given section of the flat-form material occupies between about 3% and about 10% of the overall area of the perforated sheet section. The preferred hole pattern occupies about 5% of the surface area of a given perforated sheet section. By increasing the aggregate area of the holes in a given sheet, elasticity and strength are reduced; but the density of the material can be increased proportionately to compensate and therefore maintain a necessary level of elasticity and resulting orthopedic compression force. The desired thickness of the neoprene rubber layer is about ⅛ inch. Good results are obtained with sheet thicknesses in the range of about 1/16 inch to about ¼ inch.

The preferred method for forming the hole pattern in the neoprene rubber layer is by a roller forming technique in which the roller (not shown) has a cylindrical outer surface with projecting punches in the desired hole pattern so that rolling the roller over the flat surface of the neoprene rubber sheet punches out holes in the desired pattern.

The composite material also includes a soft, flexible, resilient, porous skin-protecting inner layer 32. The presently preferred material is known by the trademark Tricot. This material is a knitted flexible and foldable, stretchable cloth fabric which is porous to air and water because of the pores inherently formed by the knitted fabric. Thus, the individual pores in the perforated neoprene rubber layer are substantially larger in area than the individual pores formed by the knitted fabric. The holes in the neoprene rubber layer are larger in area by at least an order of magnitude.

The composite material also includes a flexible and elastic, porous, protective outer layer 34 which is also made from a stretchable knitted fabric. The protective outer layer is preferably made from the material sold under the trademark Tricot.

The inner and outer layers 32 and 34 also may be made from other stretchable knitted fabrics comprising nylon, dacron or other synthetic fibers.

In the flat form material illustrated in FIGS. 3 and 4, the inner layer 32 and the outer layer 34 overlie opposite faces of the perforated neoprene base layer 28. After the neoprene rubber layer is perforated, the inner and outer fabric layers are bonded to opposite faces of the perforated base layer. A conventional adhesive provides the desired surface adhesion over the entire contacting surface areas of the perforated base layer and the adjoining knitted fabric layers 32 and 34. The adhesive does not disrupt the porosity of the perforated base layer and the knitted fabric layers 32 and 34.

The knee support made from the composite material has sufficient porosity that internal heat build-up during use is essentially avoided. One experimental test of a knee support made with the composite material 12 of this invention has demonstrated that the knee support provides sufficient ventilation to be worn of a two hour period without causing undue perspiration or other heat discomfort. By comparison, the same knee support made with the identical composite material, except that the neoprene layer was not perforated, produced perspiration almost immediately and was uncomfortable to wear for the same two hour period. The knee support of this invention is believed to be capable of being worn indefinitely without perspiration or heat discomfort problems. The level of compression support provided by the knee support of this invention also was sufficient for the intended purpose of the knee support.

The knee support is sufficiently elastic and of sufficient density to provide the compression necessary to serve as a useful knee support. Any elasticity lost by perforation of the neoprene rubber layer can be compensated for by a proportionate increase in the density of the neoprene rubber layer. In addition, the inner and outer layers 32 and 34 of the resilient, flexible knitted fabric provide resilience on their own to reinforce the elasticity of the perforated neoprene rubber, so that the composite material has the necessary level of elasticity for orthopedic use. The inner and outer layers of resilient knitted fabric also add strength to the composite material. It has been discovered that elimination of the inner fabric layer does not provide a useful orthopedic support, because direct skin contact by the larger air holes in the perforated neoprene rubber layer is discomforting to the user. The inherently formed small pores in the knitted inner fabric layer provide good porosity for air circulation. The inner resilient fabric layer enhances comfort as well as adding useful levels of elasticity and strength to the overall composite material. A preferred combination is provided by inner and outer knitted fabric layers, each having greater elasticity than the elasticity of the perforated neoprene rubber layer.

The material comprising the inner and outer layers may have different elasticity in mutually orthogonal directions. The material can be used in combination with the perforated neoprene layer so that the resulting orthopedic support has greater stretchability laterally, i.e., in a direction parallel to its top and bottom edges while the resulting support has greater resistance to stretching longitudinally, i.e., perpendicular to its top and bottom edges of the support.

FIGS. 5 through 7 illustrate further uses of the composite material 12 in orthopedic supports. FIG. 5 shows an elbow support 36 in which the composite material is folded and seamed along its length, with an intermediate seam 38 to form a somewhat L-shaped tubular elastomeric support. Top and bottom edges of the tubular support have stitched peripheral seams 40 for edge reinforcement. FIG. 6 illustrates a wrist support 42 made from the composite material 12 in which the material is folded and seamed lengthwise to form a straight tubular support having peripheral stitching 44 at its opposite ends for edge reinforcement. FIG. 7 illustrates an ankle support 46 made from the composite material. The ankle support is formed as a generally L-shaped tubular support with peripheral stitching 48 at its opposite ends, peripheral stitching 50 around an edge portion of the support that fits around the heel of the user, and intermediate stitching 52 fastening adjoining intermediate edges of the L-shaped ankle support.

These orthopedic supports can be used to provide required levels of anatomical compression support while improving air circulation to the supported area sufficient to prevent the discomfort caused by perspiration and over-heating. The improved composite material of this invention is thus responsible on its own for improving the anatomical support provided by such orthopedic supports, because the user is able to wear the support indefinitely rather than removing the support prematurely because of heat discomfort.

I claim:

1. A flexible, resilient composite material for use in making elastic orthopedic compression supports for surrounding and supporting a body part by compression, the composite material comprising:
   a porous base layer of a flexible, closed cell elastomeric foam material in thin sheet form and having a multiplicity of holes extending through the entire depth of the sheet and distributed across the surface area of the sheet, the closed cell elastomeric material having sufficient elasticity and a density of at least about ten pounds per cubic foot to provide orthopedic compression support;
   a skin-protecting first layer of a flexible, resiliently elastic porous fabric adhered to a first face of the base layer; and
   a protective second layer of a flexible, resiliently elastic porous fabric adhered to an opposite second face of the base layer, the first and second layers providing a means for reinforcing the elasticity of the porous base layer so that the composite material consisting of the combination of said base layer, first layer, and second layer maintains sufficient elasticity and density to provide a useful level of orthopedic compression support, and in which said composite material is porous to air and water passing through the depth of said composite material to provide a means of heat and moisture dissipation for the surrounded body part during use of such an orthopedic compression support.

2. The article according to claim 1 in which the first and second layers are knitted fabrics having pores naturally formed in the fabric, and the individual holes in the base layer have a substantially larger area than the area of the individual pores formed in the knitted fabric.

3. The article according to claim 1 in which the base layer is made of polychloroprene rubber.

4. The article according to claim 1 in which the holes occupy about three percent to about ten percent of the surface area of the base layer.

5. The article according to claim 4 in which the thickness of the polychloroprene rubber layer is about 1/16 to about ¼ inch.

6. An orthopedic support for supporting the knee, elbow, wrist, or the like, made from the composite material of claim 1 wherein the composite layer is overlayed and seamed to form a tubular support open at both ends.

7. An ankle support made from the composite material of claim 1 wherein the composite material is overlayed and seamed to form a generally L-shaped tubular support open at opposite ends.

8. The process according to claim 1 in which the first and second layers are adhered to opposite faces of the perforated base layer by surface adhesion over substantially the entire contacting surface areas.

9. A flexible, resilient composite material for use in making elastic orthopedic compression supports for surrounding and supporting a body part by compression, the composite material comprising:
- a porous base layer of a flexible, resilient polychloroprene rubber closed cell elastomeric foam material in thin sheet form having a multiplicity of holes extending through the entire depth of the sheet and distributed across the surface area of the sheet, in which the closed cell elastomeric material has sufficient elasticity and a density from about ten to about thirty pounds per cubic foot to provide orthopedic compression support;
- a skin-protecting first layer of a flexible, resiliently elastic porous fabric adhered to a first face of the base layer; and
- a protective second layer of a flexible, resiliently elastic porous fabric adhered to an opposite second face of the base layer, in which the resilient first and second layers provide a means for reinforcing the elasticity of the porous base layer so that the composite material consisting of the combination of said base layer, first layer, and second layer maintains sufficient elasticity and density to provide a useful level of orthopedic compression support, and in which the composite material is porous to air and water passing through the depth of said composite material, to thereby provide heat and moisture dissipation for the surrounded body part during use of such an orthopedic support.

10. The article according to claim 9 in which the holes occupy about three percent to about ten percent of the surface layer of the base layer.

11. The article according to claim 10 in which the holes are substantially uniform in size and are spaced apart substantially uniformly across the surface of the base layer.

12. The article according to claim 9 in which the thickness of the polychloroprene layer is about 1/16 to about ¼ inch thick.

13. The article according to claim 9 in which the first and second layers are adhered to opposite faces of the perforated base layer by surface adhesion over substantially the entire contacting surface areas.

14. A tubular orthopedic compression support for applying compression-type support to a surrounded body part, in which the tubular support is made from a composite material comprising:
- a porous base layer of a flexible, resilient elastomeric closed cell elastomeric foam material in thin sheet form and having a multiplicity of holes extending through the entire depth of the sheet and distributed across the surface area of the sheet, the closed cell elastomeric material having sufficient elasticity and a density of at least about ten pounds per cubic foot to provide orthopedic compression support;
- a skin-protecting first layer of a flexible, resiliently elastic porous fabric adhered to an inner face of the base layer; and
- a protective second layer of a flexible, resiliently elastic porous fabric adhered to an outer face of the base layer, in which the resilient first and second layers reinforce the elasticity of the porous base layer so that the composite material consisting of the combination of said base layer, first layer, and second layer maintains sufficient elasticity and density to provide a useful level of orthopedic compression support, and in which the composite material is porous to air and water passing through the depth of said composite material, to thereby provide a means of heat and moisture dissipation for the surrounded body part during use of such an orthopedic compression support.

15. The article according to claim 14 in which the holes occupy about 3 percent to about 10 percent of the surface area of the base layer.

16. The article according to claim 15 in which the density of the base layer is about 10 to about 30 pounds per cubic foot.

17. The article according to claim 16 in which the elastomeric closed cell base layer comprises polychloroprene rubber.

18. The article according to claim 14 in which the resulting orthopedic support has mutually orthogonal lateral and longitudinal dimensions, and in which the support has greater stretchability laterally than longitudinally.

19. The article according to claim 14 in which the first and second layers are adhered to opposite faces of the perforated base layer by surface adhesion over substantially the entire contacting surface areas.

20. A flexible, resilient composite material for use in making elastic orthopedic compression supports for surrounding and supporting a body part by compression, the composite material comprising:
- a porous base layer of a flexible, closed cell elastomeric foam material in thin sheet form and having a multiplicity of holes extending through the entire depth of the sheet and distributed across the surface area of the sheet, the closed cell elastomeric material having sufficient elasticity and density to provide orthopedic compression support;
- a skin-protecting first layer of a flexible, resiliently elastic porous fabric adhered to a first face of the base layer; and
- a protective second layer of a flexible, resiliently-elastic porous fabric adhered to an opposite second face of the base layer, the first and second layers providing a means for reinforcing the elasticity of the porous base layer, the first and second fabric layers each having an elasticity greater than the elasticity of the perforated closed cell elastomeric base layer, the composite material consisting of the combination of said base layer, first layer, and second layer maintaining a sufficient level of elasticity and density to provide a useful level of orthopedic compression support, and in which the composite material is porous to air and water passing through the depth of said composite material to provide a means of heat and moisture dissipation for the surrounding body part during use of such an orthopedic compression support.

21. The article according to claim 20 in which the base layer material has a density of at least about ten pounds per cubic foot.

22. The article according to claim 20 in which the holes occupy about three percent to about ten percent of the surface area of the base layer.

23. The article according to claim 20 in which the first and second layers are knitted fabrics having pores naturally formed in the fabric, and the individual holes in the base layer have a substantially larger area than the area of the individual pores formed in the knitted fabric.

24. The article according to claim 20 in which the first and second layers are adhered to opposite faces of the perforated base layer by surface adhesion over substantially the entire contacting surface areas.

25. A tubular orthopedic compression support for applying compression-type support to a surrounded body part, in which the tubular support is made from a composite material comprising:
   a porous base layer of a flexible, resilient elastomeric closed cell elastomeric foam material in thin sheet form and having a multiplicity of holes extending through the entire depth of the sheet and distributed across the surface area of the sheet, the closed cell elastomeric material having sufficient elasticity and density to provide a level of orthopedic compression support;
   a skin-protecting first layer of a flexible resiliently elastic porous fabric adhered to an inner face of the base layer; and
   a protective second layer of a flexible, resiliently elastic porous fabric adhered to an outer face of the base layer, in which the first and second fabric layers reinforce the elasticity of the porous base layer, and in which the first and second fabric layers each have an elasticity greater than the elasticity of the perforated closed cell elastomeric base layer, so that the composite material consisting of the combination of said base layer, first layer, and second layer maintains sufficient elasticity and density to provide a useful level of orthopedic compression support, and in which the porosity of the base layer provides heat and moisture dissipation during use of such an orthopedic compression support.

26. The article according to claim 25 in which the elastomeric base layer material has a density of at least about ten pounds per cubic foot.

27. The article according to claim 25 in which the holes occupy about three percent to about ten percent of the surface area of the base layer.

28. The article according to claim 25 in which the first and second layers are knitted fabrics having pores naturally formed in the fabric, and the individual holes in the base layer have a substantially larger area than the area of the individual pores formed in the knitted fabric.

29. The article according to claim 25 in which the first and second layers are adhered to opposite faces of the perforated base layer by surface adhesion over substantially the entire contacting surface areas.

* * * * *